United States Patent [19]

Fuhr et al.

[11] 4,116,235

[45] Sep. 26, 1978

[54] CHIROPRACTIC ADJUSTING INSTRUMENT

[76] Inventors: Arlan W. Fuhr; Warren C. Lee, both of 821 E. Bridge St., Redwood Falls, Minn. 56283

[21] Appl. No.: 808,382

[22] Filed: Jun. 20, 1977

[51] Int. Cl.² .............................................. A61F 5/00
[52] U.S. Cl. .............................................. 128/69
[58] Field of Search .................... 128/54, 68, 69, 24 R

[56] References Cited

U.S. PATENT DOCUMENTS

| | | | |
|---|---|---|---|
| 2,048,220 | 7/1936 | Redding | 128/69 |
| 2,204,259 | 6/1940 | Schuskler etal. | 128/69 |
| 2,402,901 | 6/1946 | Leddy | 128/69 |
| 2,970,592 | 2/1961 | David | 128/69 |
| 3,706,309 | 12/1972 | Toftness | 128/69 |

FOREIGN PATENT DOCUMENTS

| | | | |
|---|---|---|---|
| 321,925 | 9/1902 | France | 128/54 |

*Primary Examiner*—Lawrence W. Trapp
*Attorney, Agent, or Firm*—Clarence A. O'Brien; Harvey B. Jacobson

[57] ABSTRACT

A chiropractic adjusting instrument in the form of a manually operated and controlled device having a body contact member to apply a thrust force in a specific line of drive at a very rapid speed with this instrument replacing the previous technique of using thumb thrust having the speed generated by rapid movement of the elbows together. The instrument includes a longitudinally reciprocal spring biased member having a resilient body contact element on the end thereof and a manually movable handle connected thereto for compressing the resilient spring with adjustable means being provided for releasing the spring and contact after a predetermined compression of the spring, thereby enabling a controlled force of adjustment to be applied at a rapid speed and in a precise line of drive.

6 Claims, 2 Drawing Figures

CHIROPRACTIC ADJUSTING INSTRUMENT

BACKGROUND OF THE INVENTION

1. Field of the Invention

The present invention generally relates to a chiropractic adjusting instrument and more particularly a device which is manually operated and controlled for applying a controlled force of adjustment at a very rapid speed in a precise and specific line of drive.

2. Description of the Prior Art

Heretofore, chiropractic adjustments have usually been made by applying thumb thrust at predetermined contact points with a desired line of drive at a rapid speed, which speed is generated by the elbows of the person applying the thumb thrust being brought rapidly together. While such adjustments have produced beneficial results, the application of thumb thrust produces extreme fatigue, muscle strain, frequent elbow injury due to the elbows striking each other during rapid movement toward each other, and imprecision in the line of drive of the thumb thrust.

SUMMARY OF THE INVENTION

An object of the present invention is to provide a chiropractic adjusting instrument which provides a manually manipulatable instrument capable of providing a dynamic thrust which includes a controlled force of adjustment applied at a precise and specific line of drive at a high speed.

Another object of the invention is to provide a chiropractic adjusting instrument which includes a spring biased reciprocating member having a resilient contact element on one end thereof for engagement with the surface of the body at precise contact points with the reciprocating axis being pecisely alignable with an optimum line of drive of application of the adjustment force.

A further object of the invention is to provide a chiropractic adjusting instrument, in accordance with the preceding object, in which the spring biased reciprocating member is manually operated with adjustment means being provided for adjusting the degree of movement and compression of the spring, thereby controlling the force of adjustment applied by the instrument.

Still another object of the invention is to provide a chiropractic adjusting instrument in which the manual compression of the spring is automatically released at an adjustable point to enable the body contact element to move rapidly toward the body for extremely high speed of application of the adjustment force, with the reciprocating axis of the reciprocating member being alignable with the optimum line of force for application of the adjusting force.

Still another important object of the invention is to provide a chiropractic adjusting instrument, in accordance with the preceding objects, which is operated by one hand with fingerengaging handle means and heel of the thumb saddle or handle means thereon to enable the spring biased structure to be compressed by a squeezing operation, thus greatly facilitating the chiropractic adjustment and reducing the fatigue of the person utilizing the instrument and enabling more precise and more effective chiropractic adjustments to be administered.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
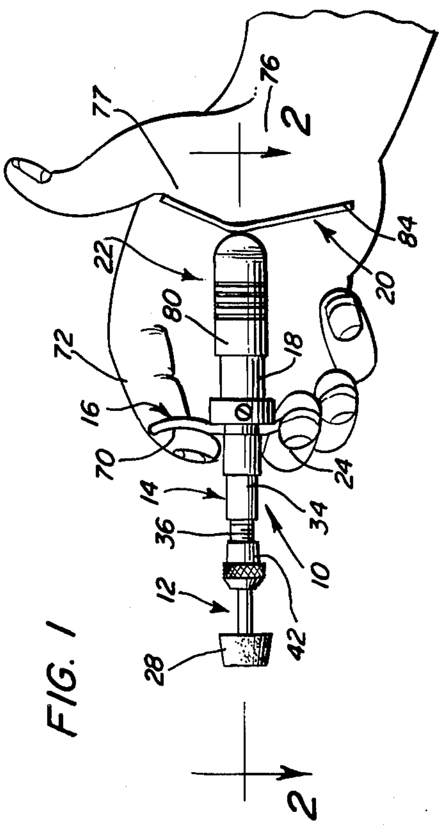
FIG. 1 is a perspective view of the chiropractic adjusting instrument of the present invention illustrating generally the manner of use of the device.
Figure 2:
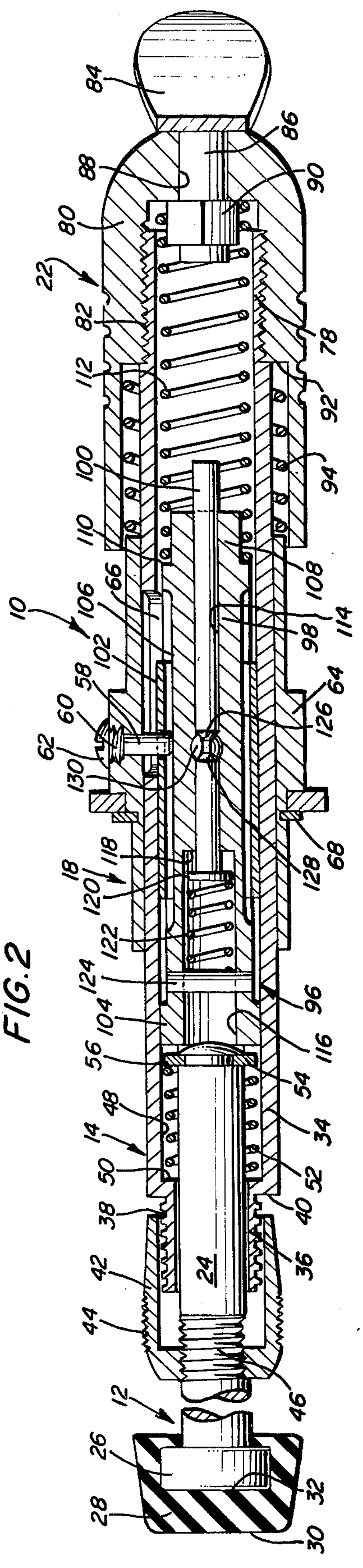
FIG. 2 is a longitudinal, sectional view of the instrument, on an enlarged scale, illustrating the association of the components thereof.

Referring now specifically to the drawings, the chiropractic adjusting instrument of the present invention is generally designated by reference numeral 10 and includes a spring biased reciprocatory thrust element 12 which is longitudinally reciprocally received within a tubular body 14 and a handle or finger-grip assembly 16 is mounted on a sleeve or main body 18 for use in conjunction with a palm or thumb heel engaging member generally designated by numeral 20 which is swivelly mounted on a tubular end cap generally designated by numeral 22.

The thrust element 12 includes a cylindrical rod 24 having a head or enlargement 26 on the outer end thereof on which is mounted a body contact member 28 which is constructed of resilient material such as rubber, plastic,, or the like, and which has a flat outer end surface 30 and a recess 32 in the inner end thereof for detachable mounting on the head or enlargement 26, thereby enabling interchange of various body contact members or replacement thereof when desired.

The cylindrical rod 24 is telescopically received in the tubular body 14 which is in the form of an elongated tube 34. The end of the tube 34 disposed toward the head 26 on the rod 24 is provided with a reduced diameter axial extension 36 which has a plurality of circumferential, parallel grooves 38 therein, with the juncture between the extension 36 and the tube 34 defining a shoulder 40 for engagement by the inner end of an adjustment knob 42 which is provided with a knurled portion 44 to enable rotation thereof and the outer end portion of the knob 42 is internally screw threaded for screw threaded engagement with a screw threaded portion 46 on the rod 24. Thus, by rotating the knob 42, it will move longitudinally of the rod 24 in order to limit the inward movement of rod 24 in relation to the tube 34 since the inner end of the knob 42 will abut the shoulder 40. When the knob 42 is rotated to its innermost position, the inner end of the knob 42 will engage the shoulder 40 to prevent any inward movement of the rod 24 in relation to the tube 34. When the knob 42 is adjusted all the way toward the head 26, maximum inward reciprocation of the rod 24 in relation to the tube 34 is permitted. The grooves 38 provide an indicator for indicating the adjusted position of the knob 42, so that the person using the device can determine and gauge the adjustment force applied through the body contact member 28.

The interior of the tube 34 is provided with a cylindrical recess 48 defining a shoulder 50 disposed radially between the recess 48 and the exterior of the reciprocatory rod 24 with the annular space therebetween receiving a compression coil spring 52 having one end abutting the shoulder 50 and the other end abutting a shoulder 54 on the inner end of the rod 24 which is defined by an enlarged cylindrical head 56 formed thereon or attached thereto after assembly of the rod 24, knob 42, tube 34, and spring 52, thereby providing an asembled unit with the maximum movement of the rod 24 being determined by the construction of the spring 52, that is, when the spring is completely compressed, further outward movement of the rod 24 is then precluded.

The main body or sleeve 18 is longitudinally slidably and non-rotatively mounted on the tube 34 by a pin 58 having a screw threaded outer end portion 60 and a head 62 which extends inwardly through a collar 64 on the exterior of the sleeve 18, through an opening in the sleeve 18 and through a slot 66 in the tube 34. The handle 16 is rotatably journaled on the sleeve 18 with one surface thereof abutting the collar 64 and the other surface engaged by a retainer ring 68 received in a groove in the sleeve 18 thus swivelly connecting the handle 16 to the sleeve 18. The handle 16 is in the form of a diametrically extending strap member having two concave finger-receiving recesses 70 on opposite sides of the longitudinal axis of the instrument and facing toward the body contact member 28 for receiving the index and middle fingers 72 and 74 of the hand 76 of a person using the device, as illustrated in FIG. 1.

The other end of the tube 34 is provided with a reduced axial, externally threaded extension 78 which is screw threadedly engaged with the end cap 22 which is in the form of a tubular member 80 that has an inner end portion telescopically receiving the end of the sleeve 18 and the tubular member 80 includes an internally threaded portion 82 spaced inwardly a substantial distance from the inner end of the tubular member 80 for screw threaded assembly with the threaded end 78 of the tube 34 so that the sleeve 18 with the handle 16 attached thereto can be reciprocated longitudinally within the inner end of the tubular member 80 with the end of the sleeve 18 being telescoped and disposed within the tubular member 80 at all times.

The palm or thumb heel engaging member 20 is an angulated transverse bar or rigid strap 84 having an integral pin 86 extending through an aperture 88 in the end of the end cap 22 which is generally semi-spherical with a retaining fastener 90 on the end of the pin or stud 86 thereby swivelly mounting the bar 84 to the end cap 22. The interior of the tubular member 80 which forms the end cap 22 is provided with a shoulder 92 adjacent the internal threads 82 for engagement with a spring 94 which extends longitudinally in encircling relation to the end of the tube 34 and abuts the end of the sleeve 18 which is telescopically received within the end of the end cap 22.

Disposed interiorly of the tube 34 is a spring compression and release assembly generally designated by numeral 96 and which includes an elongated tube 98 reciprocally receiving a rod 100 interiorly thereof and a sleeve 102 on the exterior thereof. One end of the tube 98 is provided with an external head 104 which abuts head 50 on rod 24 and defines a shoulder for limiting the movement of the sleeve 102 in one direction. The exterior surface of the tube 98 is provided with a longitudinally extending groove 106 over a major portion of its length and the end of the tube opposite from the head 104 is provided with a reduced axial extension 108 which defines a shoulder 110 for abutting one end of a compression coil spring 112. The interior of the tube 98 is provided with a longitudinal bore 114 slidably receiving the exterior of the rod 100 and a larger internal bore 116 defining a shoulder 118 at the juncture between the larger diameter bore 116 and the smaller diameter bore 114. The rod 100 is provided with an enlarged head 120 at one end thereof which is received within the larger bore 116 and which abuts the shoulder 118 in one direction of movement for limiting the movement of the rod 100. A compression coil spring 122 engages the head 120 and is received in the bore 116 with the other end of the spring 122 being engaged by a diametrically extending roll pin 124. Thus, the spring 122 biases the rod 100 so that the end thereof remote from the head 120 extends beyond the axial extension 108 on the tube 98 in concentric relationship to the spring 112 and generally in alignment with the pin 88 at the end of the end cap 22. The portion of the rod 100 received in the smaller bore 114 is provided with a peripheral recess 126 which is longitudinally elongated and provided with frusto-conical shoulders 128 forming the ends thereof where the recess or reduced diameter portion 126 joins with the rod 100. The peripheral recess 126 is alignable with a pair of diametrically arranged openings 130 in the tube 98 which receive a pair of diametrically arranged spherical balls 132 which have a diameter greater than the radial dimension between the bore 114 and the external surface of the tube 98. As illustrated, the sleeve 102 has a longitudinal dimension so that the end thereof remote from the end which engages the head 104 on the tube 98 is in alignment with the edge of the apertures or openings 130 so that the periphery of the balls 132 will preclude longitudinal movement of the sleeve 102 on the tube 98. However, when the tube 98 moves longitudinally in relation to the rod 100 so that the balls 132 become aligned with the recess 126, the balls will move inwardly into the recess thus releasing the sleeve 102 and enabling it to move longitudinally on the tube 98 and permitting the tube 98 to move in relation to the sleeve 102. The sleeve 102 is longitudinally immovably connected to the sleeve or main body 18, the collar 64 and the handle 16 by the pin 58 extending through an aperture 134 in the sleeve with the inner end of the pin 58 also extending into the groove 106 which precludes relative rotation between the sleeve 18, sleeve 102 and tube 98. Thus, the balls 132 provide a release mechanism for compression of the spring 112 and spring 94 so that as the handle 16, collar 64, sleeve 18 and tube 98 are moved with respect to the end cap 22 and bar 84 thereon, the springs will be compressed. As the balls 132 become aligned with the recess 126, they will move radially inwardly thus releasing the sleeve 102 from the handle 16 and sleeve 18 so that the compressed spring 112 will move the tube 98 and its associated structure in a direction to cause the rod 24 to move longitudinally outwardly at a rapid rate with the distance of such movement being determined by the adjustment of the knob 42. After the tube 98 has been released and the rod 24 moved to its extended position, release of the squeeze pressure on the handle 16 will enable the handle 16 and the sleeve 18 as well as the sleeve 102 to move back to its original position with the spring 94 biasing these components to the left so that the balls 132 will be cammed outwardly due to the cam surface on the frusto-conical shoulder 128 and the spring 122, thereby again latching the handle 16 and sleeve 18 as well as the sleeve 102 fixedly to the tube 98.

In use, the instrument 10 is grasped in a single hand 76 with the index finger 72 and the middle finger 74 engaged in the recesses 70 of the handle 16 and the angulated bar 84 engaged with the palm or heel of the thumb 77 as illustrated in FIG. 1, so that upon squeezing of the instrument, the bar 84 and the handle 16 will be moved towards each other. When applying the squeezing pressure, the body contact member 28 will be maintained in contact with the surface of the body and the line of thrust of the rod 24 can be precisely aligned with a desired and optimum line of drive for application of an adjustmment force to a contact point. The extent or distance of movement of the rod 24 is controlled by the adjustment knob 42 so that as the bar 84 and handle 16 are moved toward each other, depending upon the adjustment position of the knob 42, the recess 126 will become aligned with the balls 132 as the springs 112 and 94 are compressed and when the balls are aligned with the recess, the tube 98 will be released and the relatively strong spring 112 will rapidly thrust the rod 24 along the line of drive of the adjustment force, thereby providing a rapid speed thrust of a controlled distance and force in optimum relationship to the surface of the body for most effective chiropractic adjustment.

This device provides an easily manipulated structure which can be readily adjusted and controlled during application of a chiropractic adjustment thrust with the line of drive of the thrust being accurately controlled and the quantitative characteristics of the thrust being accurately controlled and providing a high speed thrust. The structure of the device is dependable and long lasting and enables the application of many chiropractic adjustments without undue fatigue with the device completely eliminating other problems encountered when utilizing the heretofore used thumb thrust technique.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A chiropractic adjusting instrument comprising a longitudinally movable thrust element having a body contact member on one end thereof, a main body having handle means thereon longitudinally slidably receiving said thrust element, an opposing handle member aligned with the thrust member and main body, compression spring means associated with the thrust member and main body to spring bias the thrust element outwardly when the handle on the main body and the handle aligned therewith are squeezed together, and release means for the spring means for automatically releasing the thrust element when the handles have been squeezed together a predetermined distance.

2. The structure as defined in claim 1 wherein said release means includes a tube having a shoulder engaged with a compression coil spring defining the spring means, a sleeve slidably mounted on said tube with the sleeve being connected with the main body and handle thereon, said tube including a pair of diametrically opposed balls received in apertures in the tube and engaged with the end of the sleeve to prevent movement of the sleeve on the tube, and means interiorly of the tube to enable inward movement of the balls when the spring has been compressed for releasing the tube from the sleeve to enable the spring to move the tube fowardly for moving the thrust element forwardly.

3. The structure as defined in claim 2 wherein the interior of the tube includes a rod having a peripheral recess therein normally longitudinally spaced from said balls, said rod being stationary and alignable with the balls when the tube is moved in a direction to compress said spring.

4. The structure as defined in claim 1 wherein said body contact member includes a resilient member enclosing the end of the thrust element.

5. The structure as defined in claim 1 wherein said main body includes an elongated tube having a shoulder on the end thereof facing the body contact member, said thrust element including a screw threaded portion receiving a knob screw threadedly thereon for engagement with the shoulder on the tube for limiting the movement of the thrust element inwardly into the tube and main body when the main body is moved in relation to the tube.

6. The structure as defined in claim 5 wherein said tube is provided with a reduced axial extension having a plurality of peripheral, parallel grooves thereon to indicate the distance the thrust element can be retracted into the tube.

* * * * *